United States Patent [19]

Falwell

[11] Patent Number: 5,904,667
[45] Date of Patent: May 18, 1999

[54] ROTATABLE CONTROL MECHANISM FOR STEERABLE CATHETER

[75] Inventor: Gary S. Falwell, Manchester, N.H.

[73] Assignee: C.R. Bard, Inc., Murray Hill, N.J.

[21] Appl. No.: 08/818,353

[22] Filed: Mar. 17, 1997

[51] Int. Cl.⁶ .................................................. A61M 37/00
[52] U.S. Cl. .............................................. 604/95; 600/146
[58] Field of Search .............................. 604/95, 280–282, 604/264; 600/131, 139, 146, 147

[56] References Cited

U.S. PATENT DOCUMENTS

| | | | |
|---|---|---|---|
| 3,921,295 | 11/1975 | James ...................................... | 32/14 E |
| 5,358,478 | 10/1994 | Thompson et al. . | |
| 5,383,852 | 1/1995 | Stevens-Wright . | |
| 5,395,327 | 3/1995 | Lundquist et al. . | |
| 5,462,527 | 10/1995 | Stevens-Wright et al. ............... | 604/95 |
| 5,531,687 | 7/1996 | Snoke et al. .............................. | 604/95 |
| 5,676,653 | 10/1997 | Taylor et al. .............................. | 604/95 |

FOREIGN PATENT DOCUMENTS

| | | | |
|---|---|---|---|
| 0 521 595 A2 | 1/1993 | European Pat. Off. | ....... A61M 25/01 |
| 0 521 595 A3 | 1/1993 | European Pat. Off. | ....... A61M 25/01 |
| 0 585 473 A1 | 3/1994 | European Pat. Off. | ....... B62M 24/04 |

*Primary Examiner*—John D. Yasko
*Attorney, Agent, or Firm*—Darby & Darby, P.C.

[57] ABSTRACT

A steerable catheter control mechanism comprises a rotatable driver and a deflection device responsive to the driver to selectively secure a pair of control wires. The control wires are positioned such that rotation of the driver reduces the effective deflection device radius while loading a selected wire in tension, thereby maintaining a relatively constant torque acting on the driver and minimizing operator fatigue. The deflection device is also responsive to the driver to selectively place one of the control wires in tension while maintaining the other wire in a static state thereby minimizing control wire fatigue.

23 Claims, 4 Drawing Sheets

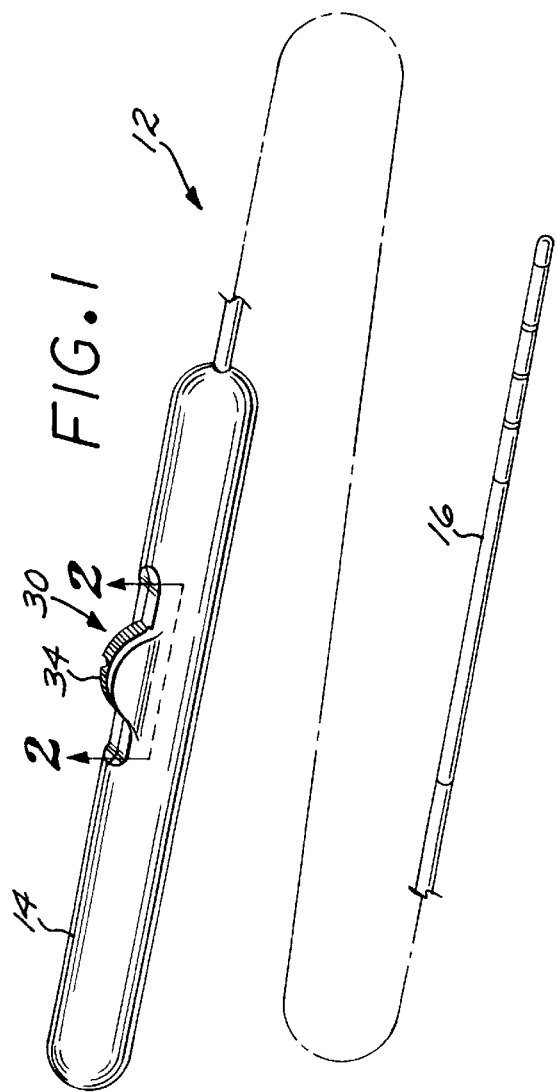
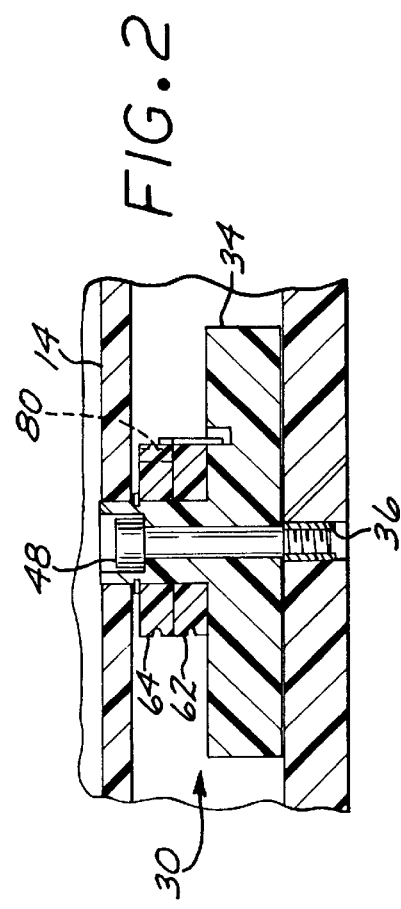

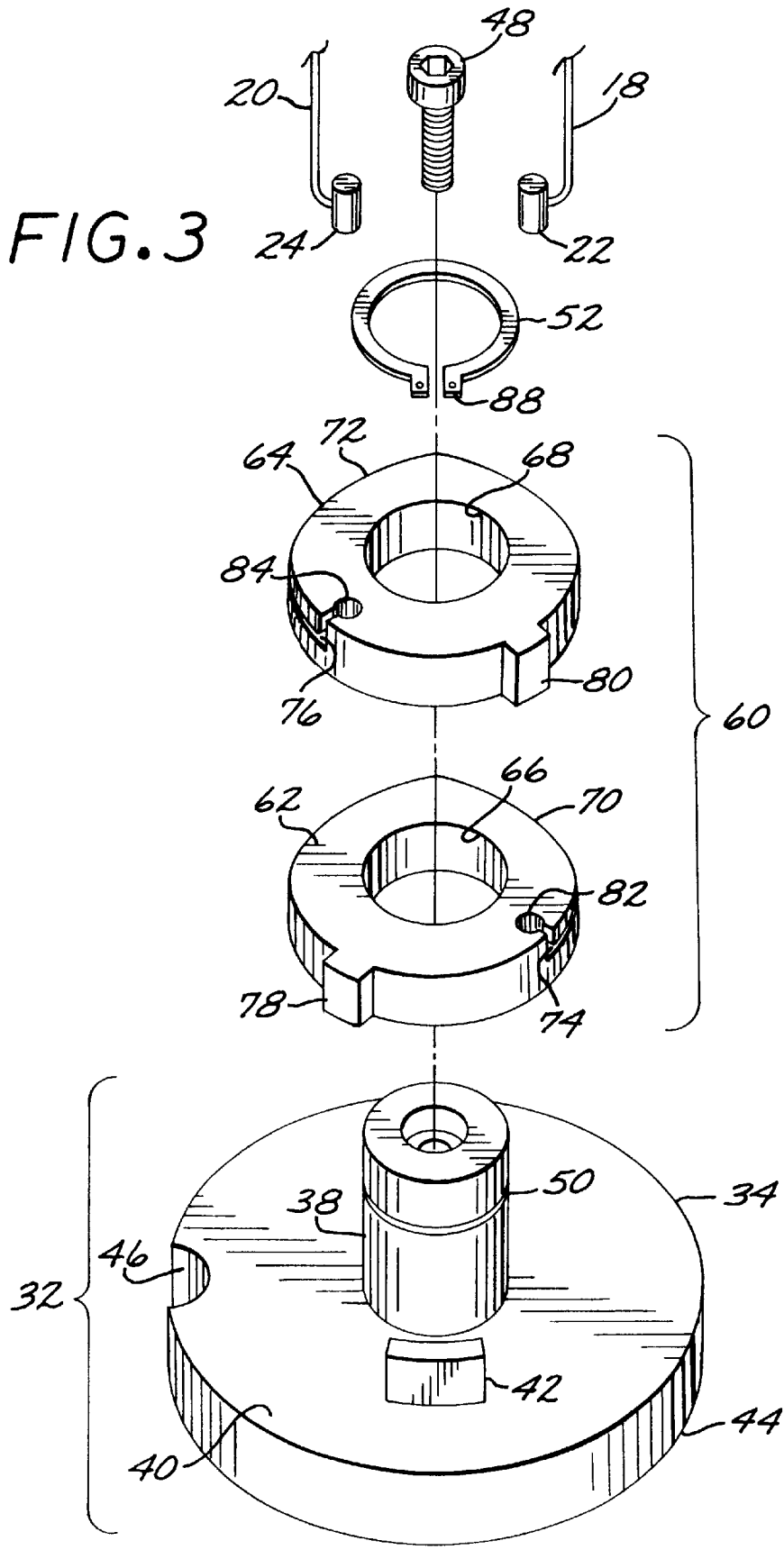

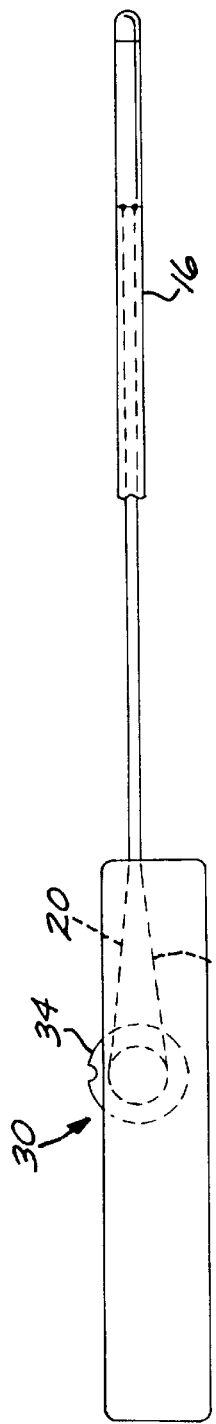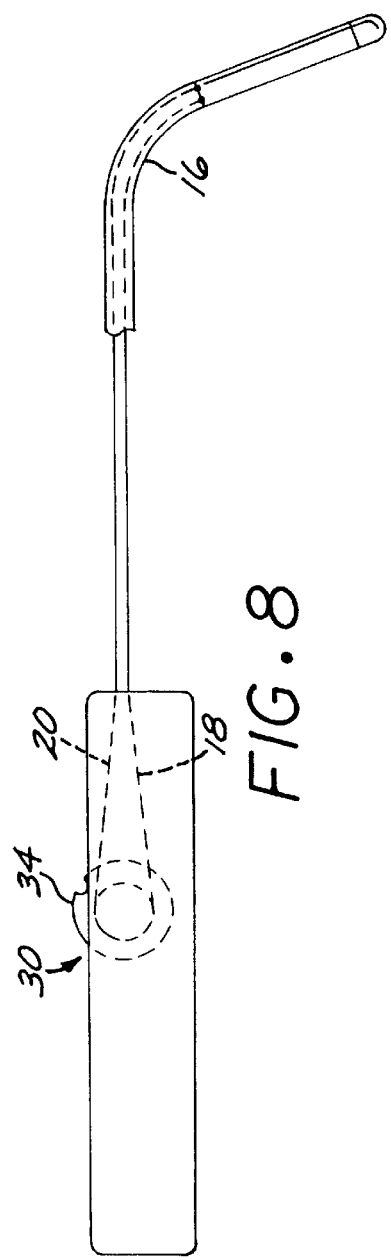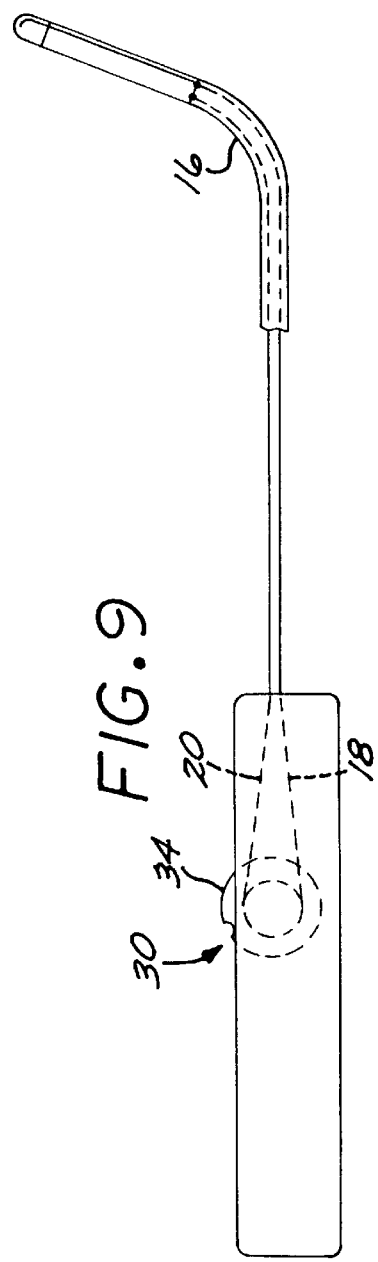

ROTATABLE CONTROL MECHANISM FOR STEERABLE CATHETER

FIELD OF THE INVENTION

The invention relates to the field of steerable catheters and, more particularly, to a rotatable control mechanism for use with a steerable catheter to minimize control wire fatigue.

BACKGROUND OF THE INVENTION

Physicians must often commonly access the interior of the human body to perform detailed tissue diagnoses or surgical procedures. As an indispensable tool for such procedures, catheters conveniently provide a means of access without the invasive trauma often associated with, for example, open heart surgery. Inserted within the body's vasculature, such catheters must be precisely controllable to position, as examples, ablation electrodes or imaging probes proximate specific tissues of interest.

To enable precision catheter manipulation within a vasculature, those skilled in the art have implemented control wire mechanisms that selectively "steer" the distal tip of the catheter while the operator inserts the device into the body. Such mechanisms typically include a pair of control wires with distal ends anchored to specific locations at the distal tip of the catheter body corresponding to predetermined deflectional movement. The proximal ends of the wires are mounted to a rotatable actuator that responds to the operator to place one of the wires in tension, pulling at the catheter end for deflection in a first direction, while simultaneously compressing, or buckling, the other wire. An example of such a catheter configuration incorporating such a control mechanism may be found in U.S. Pat. No. 5,383,852, assigned to the assignee of the present invention.

While such devices generally provide a relatively high degree of directional deflection for the catheter tip, over a relatively short period of time the repetitive tensioning and buckling of the control wires may cause control wire fatigue. As a result, the operable lifespan of the device may be substantially shortened.

To address the problem of wire fatigue in a steerable catheter, one proposal, by Thompson (U.S. Pat. No. 5,358,478), discloses a rotatable cam formed with a first cam surface of a first radius on the right side of an asymmetric cam wheel. The left side of the cam wheel is formed with a second cam surface of a second different radius. The rotatable cam includes threaded holes to threadably receive adjustable stops. The proximal ends of the first and second steering cables pass through central openings formed in the respective stops and are attached to respective steering wire terminals.

During operation, by urging the rotatable cam to the left, the second steering wire stop bears against the left terminal block and cam surface. This movement tensions the second steering cable to deflect the catheter tip to the left, while the first steering cable remains relaxed. Likewise, urging of the rotatable cam to the right places the first steering cable in tension while the second steering cable remains relaxed.

While this device works well for its intended purposes, operators may experience fatigue in manipulating the catheter over prolonged periods of time. This may occur because the radius of the cam wheel with respect to the loaded control wire increases as loading increases. The additional loading causes more torque at the actuator, contributing to operator fatigue within a relatively short time.

A second proposal for addressing control wire fatigue, by Lundquist (U.S. Pat. No. 5,395,327), discloses independently tensioning a first steering cable while simultaneously keeping a second steering cable at rest. The device includes two separate cam wheels disposed in-line along the catheter body and attached to respective steering cables. The cam wheels are independently attached to separate operator knobs. During use, the operator rotates one wheel to place one wire in tension and bend the catheter tip accordingly. To effect deflection in another direction, the operator switches to the other knob. As loading increases on each wheel from the tensioning of the respective cables, the torque on the respective knobs correspondingly increases. As a result, operator fatigue can occur within a relatively short period of time. Moreover, because of the dual knob arrangement, operation of the device is somewhat more complex than a unitary knob configuration.

Therefore, there is need for an improved steerable catheter control mechanism which minimizes control wire fatigue. Moreover, a need also exists for a control mechanism capable of minimizing operator fatigue. The control mechanism of the present invention satisfies these needs.

SUMMARY OF THE INVENTION

The control mechanism of the present invention provides the capability of selectively placing one control wire in tension while simultaneously maintaining the other wire in a static state. By maintaining the static state, control wire fatigue due to repetitive buckling is substantially minimized. Moreover, the present invention also minimizes operator fatigue by maintaining the torque on the actuator at a constant level during increased loading of the control wire.

To realize the advantages identified above, the control mechanism of the present invention, according to one embodiment, manipulates a pair of control wires having respective distal portions anchored to the distal end of a steerable catheter. More specifically, the control mechanism includes a driver rotatable about a central axis and a deflection device coupled to the driver to selectively secure the control wire proximal ends. The deflection device is formed with an eccentric deflection surface for tangentially engaging the control wires and includes a reducible radius in response to driver rotation from a predetermined neutral position. The deflection device is operative, as the driver rotates in a selected radial direction, to place a selected one of the wires in tension as the radius decreases and correspondingly reduce torque acting upon the driver, thereby minimizing operator fatigue.

Other features and advantages of the present invention will be apparent from the following detailed description when read in conjunction with the accompanying drawings.

BRIEF DESCRIPTION OF THE DRAWINGS

FIG. 1 is a perspective view of a steerable catheter implementing a rotatable control mechanism according to one embodiment of the present invention;

FIG. 2 is a partial cross sectional view along line 2—2 of FIG. 1;

FIG. 3 is an exploded perspective view of a rotatable control mechanism according to one embodiment of the present invention;

FIGS. 7–9 are diagrammatic illustrations showing distal bending movement of the catheter distal end corresponding to the actuation of the control mechanism shown in FIGS. 4–6.

DETAILED DESCRIPTION OF THE PREFERRED EMBODIMENTS

Figure 4:
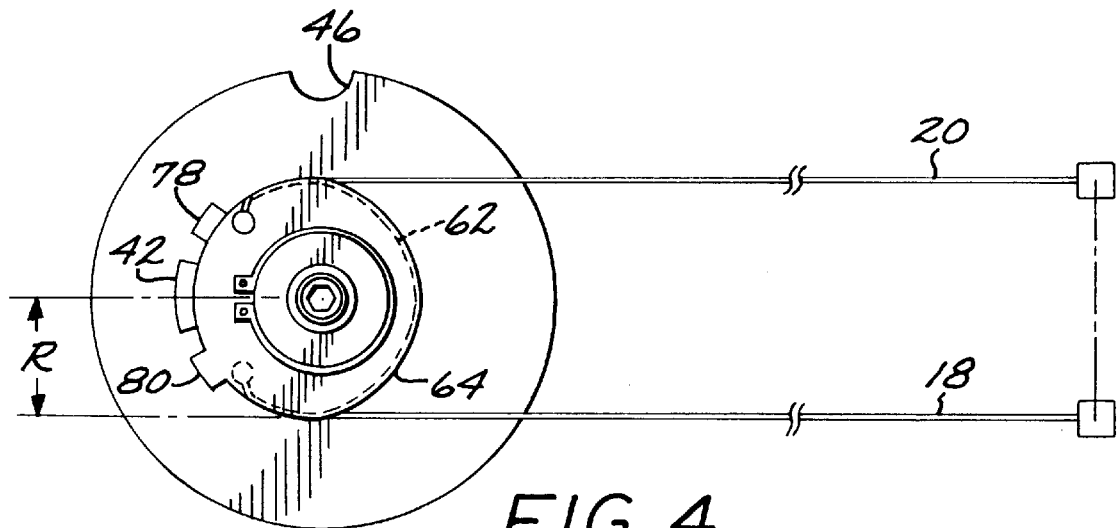
FIG. 4 is a diagrammatic illustration of the control mechanism in a neutral position.

Steerable catheters provide physicians, or operators, an indispensable tool for conveniently accessing the interior of the human body without the level of trauma commonly associated with more invasive surgical techniques. As shown by example in FIG. 1, a steerable catheter according to one embodiment of the present invention, and generally designated 12, includes an elongated hollow handle 14. The interior of the handle defines a compartment 15 for housing a control mechanism according to the present invention, and generally designated 30.

Further referring to FIG. 1, a narrow flexible shaft 16 projects longitudinally from one end of the handle for intravascular insertion. The shaft is typically formed from a polyurethane material of a predetermined stiffness and includes one or more longitudinally extending lumens (not shown) for running two or more steering or control wires 18 and 20 (FIGS. 7–9) therethrough.

To effect precision steering of the catheter distal end 16 during intravascular insertion the control wires 18 and 20 run longitudinally through the catheter shaft lumen and respectively mount to specific distal points in the shaft such that tension on a selected wire deflects the shaft in a predictable direction. The proximal ends of the control wires typically terminate in respective pins 22 and 24 (FIG. 3) for anchoring to the control mechanism 30 inside the compartment 15.

Referring now to FIGS. 2 and 3, the control mechanism of the present invention 30 incorporates a rotatable driver 32, and a deflection device 60 having a radius reducible in response to actuation of the driver and capable of selectively placing one of the two control wires in tension while maintaining the other wire in a static state.

Further referring to FIGS. 2 and 3, the driver 32 comprises a circular thumbwheel 34 formed centrally with a cylindrical spindle 38 that projects axially from an inboard flange 40 of the thumbwheel. The spindle includes a centrally formed axial throughbore for receiving a threaded fastener 48 that rotatably mounts the driver to a threaded bore formed in the compartment 15. An annular channel 50 externally formed on the spindle provides a radial slot for affixing a spindle stop 52. An axially projecting drive pin 42 is disposed a predetermined radial distance from the spindle 38, and provides an important feature by selectively actuating the deflection device 60 to produce tension on one of the wires according to the directional rotation of the thumbwheel.

For maximal touch control, the thumbwheel 34 is formed with a finely serrated outer periphery 44. Additionally, to conveniently set the control mechanism 30 in a neutral position, a coarse locator notch 46 is configured into the wheel to open vertically and present an identifiable marker as "neutral".

The deflection device 60 comprises a pair of independently actuable eccentric pulleys 62 and 64 respectively formed with axial openings 66 and 68 to receive the spindle 38 in coaxial relationship. The pulleys are formed as a mirrored pair, with respective eccentric deflection surfaces 70 and 72 that respectively define a variable radius relative to the center of the spindle, which defines a central axis. Formed into the periphery of the deflection surfaces are respective grooves 74 and 76 to tangentially engage and wind the respective control wires 18 and 20 during operation.

A particularly advantageous feature of the present invention involves the orientation of the deflection surfaces 70 and 72 with respect to the control wires such that actuation of a selected pulley reduces the radius between the point of engagement with the control wire and the central axis. By reducing the radius approximately by half, the inventor has discovered that the torque acting on the thumbwheel may be maintained substantially constant under proportionately increasing tensile loads on the selected pulley, thereby correspondingly decreasing operator fatigue.

The pulleys 62 and 64 are further formed with respective actuator tabs 78 and 80 raised radially outwardly from the respective pulley backsides. The respective tabs are offset in a mirrored relationship, when assembled to the thumbwheel, to straddle the drive pin and effect selective actuation of a respective pulley in response to directional advancement of the drive pin. Axial apertures 82 and 84 formed proximate the tabs serve to radially anchor the respective control wire pins 22 and 24.

Assembly of the control mechanism 30 comprises fairly straightforward techniques well known to those skilled in the art and begins by first mounting the spindle to the thumbwheel 34. With the catheter shaft placed in a substantially straight orientation, the respective control wire pins 22 and 24 are then inserted into the complementally formed apertures 82 and 84 in the respective pulleys. The spindle may then be coaxially inserted through the respective pulleys with the drive pin 42 positioned midway between the two symmetrically offset tabs 78 and 80. To maintain axial alignment, the spindle stop 52 nests securely within the annular channel 50 and includes a radially projecting flange 88 to minimize relative axial movement between the pulleys.

Once the control mechanism sub-assembly is completed, the manufacturer may then proceed to install the sub-assembly into a suitable housing or handle as is well known in the art. Typically, the control mechanism will be installed such that the thumbwheel projects outwardly from the handle to effect unobstructed operator access. Following installation, the control mechanism is calibrated with respect to the catheter shaft such that the "neutral" position indicator 46 corresponds to the shaft being in a relaxed state with the respective control wires in a static state. A portion of the calibration includes orienting the respective pulleys such that the point of contact with the respective wires, as shown in FIG. 4, forms a radius "R" with respect to the central axis.

During operation, the catheter assembly 12 will normally be set to the calibrated relaxed or neutral configuration, such as that shown in FIGS. 4 and 7. Visual confirmation of the neutral state may be made by simply referring to the position of the formed notch 46, normally opening vertically. The catheter may then be inserted into the vasculature of interest.

Figure 5:
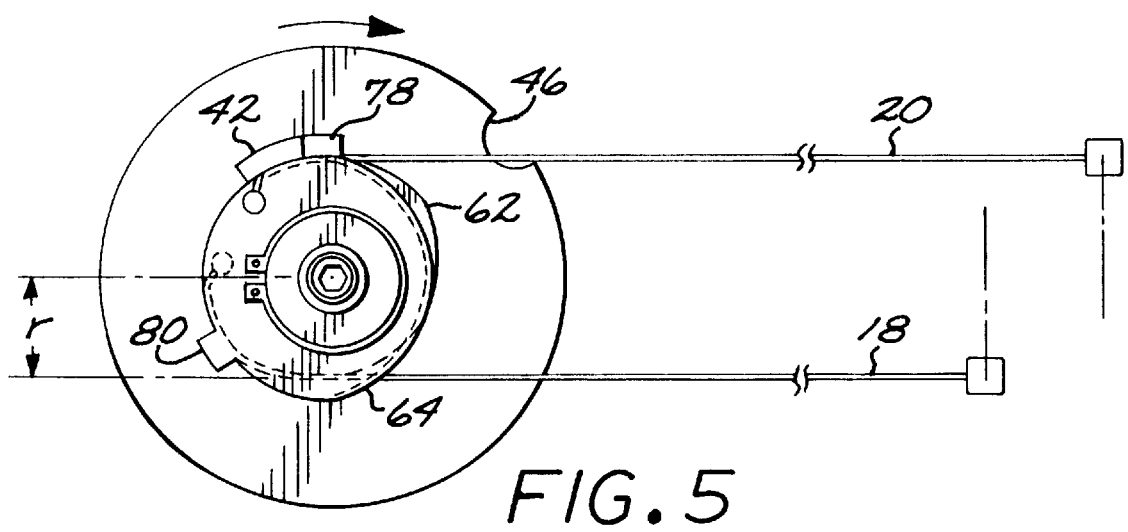
FIGS. 5–6 are diagrammatic illustrations showing rotary actuation of the control mechanism.

Once inserted into the body, manipulation of the distal tip of the catheter may be effected by rotating the thumbwheel a direction corresponding to the desired direction of deflection. Referring now to FIG. 5, a clockwise rotation of the wheel radially displaces the drive pin 42 to engage the upper tab 78 of the pulley 62 and effect actuation in the direction of thumbwheel rotation. Rotation of the pulley causes a winding action on the anchored lower wire 18 and orients the deflection surface 70 into tangential engagement with the wire to place it in tension. The action of the deflection surface effectively pulls on the wire to correspondingly deflect the distal tip of the catheter shaft 16, as shown in FIG. 8.

In operation, actuation of the thumbwheel produces leverage of a magnitude corresponding to the pulley radius between the point of engagement with the tensioned wire, and the central axis. The length of the lever arm, or radius, contributes to the torque experienced by the operator in actuating the thumbwheel. Although continued rotation of the pulley increases the tensile load on the wire, because the radius of the pulley decreases to a radius "r" (FIG. 5) with continued rotation, the torque experienced at the thumbwheel resulting from the combined effects of the additional tension and reduced radius remains substantially constant. Thus, over a period of time, operator fatigue from varying levels of torque is substantially reduced.

While the selected pulley actuation from the thumbwheel subjects the lower wire 18 to a tensile force, the upper wire 20, being anchored to the undisturbed pulley 64, remains in a static state. The independent relationship between the two pulleys and the unidirectional interplay between the respective drive tabs and the drive pin preserves the static nature of the other pulley, and consequently, the wire. This feature virtually eliminates compression or buckling of the non-selected wire and substantially inhibits premature wire fatigue due to such buckling.

Figure 6:
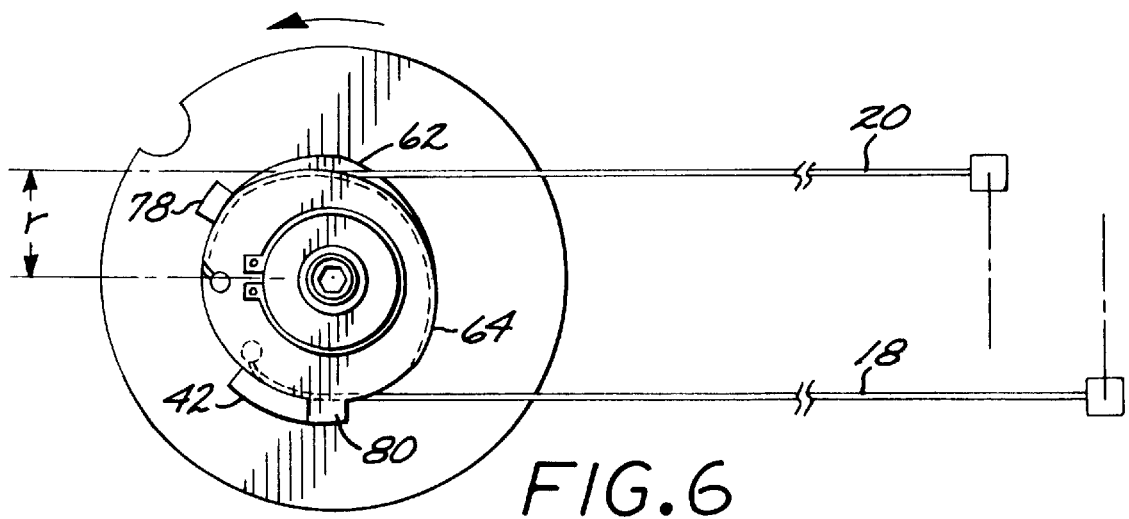

To manipulate the catheter tip in another direction, the operator merely rotates the thumbwheel rearwardly such that the guide pin retracts from the upper pulley tab 78. During retraction, the built up tension in the wire serves as a biasing means to return the pulley 62 back to its calibrated neutral, or static state. Continued rearward rotation of the thumbwheel then directs the drive pin 42 into contact with the lower pulley tab 80 to actuate the other pulley 64. FIGS. 6 and 9 illustrate this activity, with results similar to that discussed above.

While the control mechanism of the present invention has been described as the sole manipulation device for the catheter shaft, it will be understood that one or more additional control mechanisms may be implemented to complement the invention. For example, the capabilities of the present invention may be supplemented by a slidable control mechanism (not shown) disposed proximate the thumbwheel to effect steerable control over additional control wires routed through the shaft and anchored to the shaft distal end. A suitable slidable control mechanism is disclosed in the applicant's copending application Ser. No. 08/818,352 filed on Mar. 17, 1997, assigned to the assignee of the present invention, and hereby incorporated by reference.

Those skilled in the art will appreciate the many benefits and advantages afforded by the control mechanism of the present invention. Of significant importance are the reducible radii of the respective pulley deflection surfaces that provide a relatively constant torque on the thumbwheel even with increases in tensile loading of the selected wire. By maintaining a constant level of torque, operator fatigue is significantly minimized.

In addition to minimizing operator fatigue, the present invention also significantly reduces premature wire fatigue due to compression or buckling of the non-loaded wire during operation. This feature is realized by implementing independently rotatable pulleys responsive to directional displacement of the thumbwheel.

While the invention has been particularly shown and described with reference to the preferred embodiments thereof, it will be understood by those skilled in the art that various changes in form and detail may be made therein without departing from the spirit and scope of the invention.

What is claimed is:

1. A control mechanism for manipulating a pair of control wires having respective distal portions anchored to the distal end of a steerable catheter corresponding to predetermined directional deflections of said catheter, said control mechanism including:

a driver rotatable about a central axis; and a deflection device coupled to said driver to selectively secure said control wire proximal ends and formed with an eccentric deflection surface for tangentially engaging said control wires, said surface having a reducible radius in response to driver rotation from a predetermined neutral position, said device operative, as said driver rotates a selected radial direction, to place a selected one of said wires in tension as said radius reduces and correspondingly decrease torque acting upon said driver thereby minimizing operator fatigue.

2. A control mechanism according to claim 1 wherein:

said surface is formed such that rotation of said driver decreases said radius proportionately to said tension to maintain a constant torque on said driver.

3. A control mechanism according to claim 1 wherein:

said driver comprises a manually controllable actuator; and said deflection device comprises at least one eccentric element responsive to rotary movement of said actuator.

4. A control mechanism according to claim 3 wherein:

said actuator comprises a circular thumbwheel.

5. A control mechanism according to claim 3 wherein:

said at least one eccentric element comprises at least one eccentric cam pulley.

6. A control mechanism according to claim 1 wherein:

said deflection device comprises a pair of independently rotatable eccentric cam pulleys disposed coaxially on said driver central axis and selectively responsive to rotation of said driver to place a selected one of said wires in tension.

7. A control mechanism according to claim 6 wherein:

said thumbwheel includes a formed pin disposed radially outwardly from said central axis; and said pulleys include respective formed tabs projecting radially outwardly to selectively engage said pin as said thumbwheel rotates a selected direction thereby placing a selected one of said wires in tension.

8. A control mechanism according to claim 1 wherein:

said deflection device is formed with at least one fastener to selectively secure said control wires.

9. A control mechanism according to claim 8 wherein:

said fasteners comprise unidirectional stops, when said driver rotates, to pull a selected one of said wires in tension while simultaneously maintaining said other wire in a static state.

10. A control mechanism for manipulating a pair of control wires having respective distal portions anchored to the distal end of a steerable catheter corresponding to predetermined directional deflections of said catheter, said control mechanism including:

a driver rotatable about a central axis; and a deflection device coupled to said driver and comprising a pair of independently rotatable pulleys disposed coaxially on said central axis, said pulleys selectively responsive to directional rotation of said driver, as said driver rotates a selected radial direction, to place a selected one of said wires in tension while the other of said pulleys maintains said other of said wires in a static state thereby minimizing control wire fatigue.

11. A control mechanism according to claim 10 wherein:

said driver comprises a manually controllable actuator; and said pulleys are selectively responsive to directional rotation of said actuator.

12. A control mechanism according to claim 11 wherein:

said actuator comprises a circular thumbwheel.

13. A control mechanism according to claim 10 wherein:

said pulleys comprise respective eccentric cam pulleys.

14. A control mechanism according to claim 12 wherein:

said thumbwheel includes a formed pin disposed radially outwardly from said central axis; and said pulleys include respective formed tabs projecting radially outwardly to engage said pin as said actuator rotates a selected direction thereby placing a selected one of said wires in tension.

15. A control mechanism according to claim 12 wherein:

said eccentric pulleys are each formed with an eccentric deflection surface for tangentially engaging said control wires, said surface having a reducible radius in response to rotation of said actuator from a predetermined neutral position, said pulleys operative, as said driver rotates a selected radial direction away from said neutral position, to place a selected one of said wires in tension as said radius reduces and correspondingly decreases torque acting upon said driver thereby minimizing operator fatigue.

16. A control mechanism according to claim 15 wherein:

said respective deflection surfaces are formed such that rotation of a selected one of said cams decreases said radius proportionately to said tension to maintain a constant torque on said driver.

17. A steerable catheter for controllable manipulation through a vasculature, said catheter comprising:

a shaft having a distal end;

at least two control wires having distal portions respectively anchored to said shaft distal end and corresponding to predetermined directional deflections of said shaft; and a control mechanism mounted upon the shaft, said control mechanism including a driver rotatable about a central axis; and a deflection device coupled to said driver to selectively secure said control wire proximal ends, said device comprising a pair of independently rotatable eccentric cam pulleys disposed coaxially on said central axis and selectively responsive to rotation of said driver, said pulleys each formed with a deflection surface for tangentially engaging said control wires, said surface having a reducible radius in response to driver rotation from a predetermined neutral position, said device operative, as said driver rotates a selected radial direction, a selected one of said pulleys places a selected one of said wires in tension while said other of said pulleys maintains said other of said wires in a static state and continued rotation of said actuator reduces said radius to correspondingly decrease torque acting upon said driver.

18. A method of controlling a steerable catheter to minimize operator fatigue, said catheter having a control mechanism including a driver rotatable about a central axis and a deflection device formed with an eccentric deflection surface having a reducible radius in response to driver rotation from a predetermined neutral position, and a pair of control wires having distal portions anchored to the distal end of said catheter and proximal portions selectively fastened to said deflection device, said method including the steps of:

engaging a selected one of said control wires tangentially with said deflection device in response to rotation of said driver; and reducing said radius through continued rotation of said driver thereby decreasing the torque acting on said actuator and correspondingly reducing operator fatigue.

19. A method according to claim 18 wherein:

said reducing step includes reducing said effective radius proportionately to the tension in said applying step to maintain a constant torque on said actuator.

20. A method according to claim 18 and further including the step of:

maintaining said other of two control wires in a static state simultaneously with said applying step to minimize wire fatigue.

21. A method of controlling a steerable catheter to minimize control wire fatigue, said catheter having a control mechanism including a driver and a pair of independently rotatable pulleys disposed in coaxial relationship with the driver and including respective control wire fasteners to secure a pair of control wires having distal portions anchored to the distal end of said catheter and proximal portions selectively fastened to said respective pulleys, said pulleys selectively responsive to directional rotation of said driver, said method including the steps of:

applying tension to one of said control wires by rotating said driver to selectively rotate one of said pulleys; and maintaining said other of two control wires in a static state simultaneously with said applying step to minimize wire fatigue.

22. A method according to claim 21 wherein said pulleys each are formed with an eccentric deflection surface having a reducible radius in response to driver rotation from a predetermined neutral position, said method further including the step of:

reducing said radius through continued rotation of said actuator thereby decreasing the torque acting on said actuator and correspondingly reducing operator fatigue.

23. A method according to claim 22 wherein:

said reducing step includes reducing said effective radius proportionately to the tension in said applying step to maintain a constant torque on said actuator.

\* \* \* \* \*